United States Patent [19]

Bruey

[11] Patent Number: 4,990,514

[45] Date of Patent: Feb. 5, 1991

[54] NON-PARTICULATE, NON-FLOWABLE, NON-REPELLANT INSECTICIDE-BAIT COMPOSITION FOR THE CONTROL OF COCKROACHES

[75] Inventor: Francis J. Bruey, Bloomfield, N.J.

[73] Assignee: The Clorox Company, Oakland, Calif.

[21] Appl. No.: 42,500

[22] Filed: Apr. 27, 1987

[51] Int. Cl.$^5$ .................... A01N 37/52; A01N 43/50; A01N 43/54; A01N 43/62
[52] U.S. Cl. ..................................... 514/275; 424/78; 424/84; 514/218; 514/392; 514/632
[58] Field of Search ............... 514/275, 632, 218, 392; 414/84, 78

[56] References Cited

U.S. PATENT DOCUMENTS

| | | | |
|---|---|---|---|
| 3,878,261 | 4/1975 | Tomenfcik | 540/553 |
| 4,087,525 | 5/1978 | Lovell | 514/219 |
| 4,163,102 | 7/1979 | Lovell | 544/330 |
| 4,353,907 | 10/1982 | Lovell | 514/275 |
| 4,514,960 | 5/1985 | Sears | 514/183 |
| 4,657,912 | 4/1987 | Suzuki et al. | 424/84 |
| 4,663,341 | 5/1987 | Jacobson | 514/272 |

*Primary Examiner*—Allen J. Robinson
*Attorney, Agent, or Firm*—Charles J. Fickey; Harry A. Pacini

[57] ABSTRACT

A solid, non-particulate, non-flowable, non-repellant insecticide bait composition for consumer household control of cockroaches, comprises an insecticide compound, a food attractant system, and a flowable binder, wherein said composition is more readily flowable and process able.

7 Claims, No Drawings

NON-PARTICULATE, NON-FLOWABLE, NON-REPELLANT INSECTICIDE-BAIT COMPOSITION FOR THE CONTROL OF COCKROACHES

The present invention relates to solid, non-particulate, non-flowable, non-repellant, fully edible insecticide-bait compositions for the consumer control of cockroaches. More particularly, it relates to insecticide-bait compositions comprising an insecticide compound, a specific food attractant system, and a flowable binder. A preservative is optionally added to the composition.

In copending, commonly assigned application Ser. No. 628,128, filed Jul. 9, 1984, now abandoned and refiled as Ser. No. 933,331, filed Nov. 19, 1986, now abandoned and refiled as Ser. No. 183,283, filed Apr. 11, 1988, now U.S. Pat. No. 4,845,013, a bait was described similar to the above, except that oatmeal was used as a binder.

The bait of the copending application is a highly viscous, quick-setting formulation with a batch pot life of about four hours. The bait then becomes hard. This requires production to prepare small batches to make frequent quality assurance sampling, equipment cleaning and disposal of large amounts of unused product, thus resulting in much inconvenience and, as noted, greater cost.

Oatmeal is used as a binder in the formulation of the copending application. It is not believed to be a preferred food material, or even perceived by the target insects. Oatmeal also has several disadvantages: (1) it contains high levels of microorganisms and, thus, has to be irradiated by gamma rays; (2) it requires dusty grinding for uniformity; and (3) it causes the formulation to harden in about four hours. Thus, a formulation which does not require oatmeal as a binder, but has similar efficacy, would be very advantageous.

It has now been found that replacing oatmeal with Elmers glue, a polyvinyl acetate emulsion-based glue, resulted in acceptable bait efficacy, longer pot life and ease of manufacturing. Other substitutes for oatmeal are acetate emulsion-based glue, polyvinyl acetate emulsion, natural glue (beef collagen), Knox gelatin, Carragennan, and water-absorbing polymers. The last two have the advantage of being used as a potential use-up signal since they shrink with loss of moisture.

Elmers glue is an adhesive containing polyvinyl acetate resin emulsion, polyvinyl alcohol, plasticizer, solvent, defoamer, preservative and filler. A stable emulsion product with glue: food attractant (sugar) ratio of 1:1.6 can be formulated without additional emulsifier. Adding more polyvinyl alcohol emulsifier helps to stabilize a 1:1.80 ratio product. The emulsion is stable for 2-3 days and can be easily redispersed. This emulsion can also be foamed to give a low density bait. Efficacy of this product is statistically the same as that of copending application Ser. No. 628,128 under laboratory conditions.

Elmers glue is a commercial product of Borden, Inc. Ingredients, such as plasticizer, defoamer, solvent, and filler are unnecessary in the present formulation. Polyvinyl acetate emulsion (W. R. Grace) may be used as the bait matrix and a product with glue: sugar ratio of 1:2 can be formulated, using polyvinyl alcohol as an emulsifier. The emulsion is stable for more than a week and can be redispersed to give a homogeneous emulsion. A gram of the product can be dispensed into the bait well and can be set at room temperature within two to six hours. The binder is used in the amount of about 30 to 60% of the composition.

A suitable insecticide is a pentadierone hydrozone.

Pentadiene-3-one substituted amidinohydrazones are described by Tomcufcik, U.S. Pat. No. 3,878,201, as anti-malarial and anti-tubercular agents. Lovell, U.S. Pat. Nos. 4,087,525 and 4,163,102—the disclosures of which are incorporated hereby by reference thereto, describes the use of these compounds as insecticides. The insecticide compounds of the Lovell patents are generally represented by the formula:

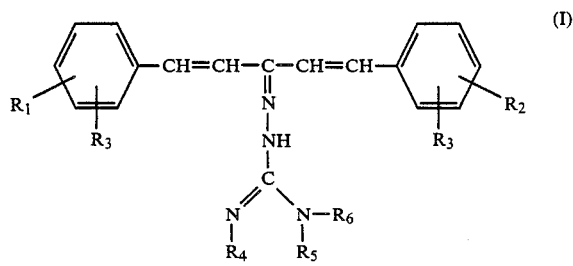

wherein $R_1$ and $R_2$ each represent hydrogen, halogen, the group $-CF_3$, $C_1-C_4$ alkyl, $C_1-C_4$ alkoxy, or $C_1-C_4$ alkylthio; $R_3$ is hydrogen or methyl, provided that when $R_3$ is methyl both $R_1$ and $R_2$ are also methyl; $R_4$ and $R_5$ represent hydrogen, $C_1-C_4$ alkyl or, when taken together, an alkylene group of 2 to 6 carbon atoms, methyl or phenyl alkylene group of 2 to 4 carbon atoms or 1,2-cyclohexylene; $R_6$ is hydrogen or $C_1-C_4$ alkyl; and salts thereof.

Particularly useful compounds are those represented by the formula:

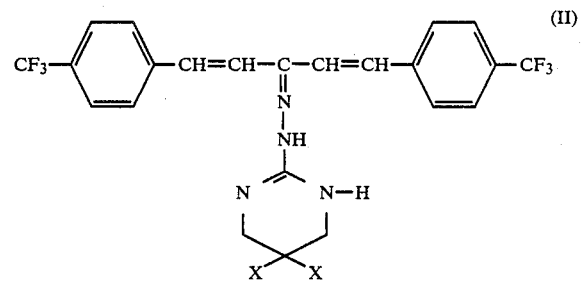

wherein X is hydrogen or methyl. The efficacy of the compounds represented by formulas (I) and (II) against a variety of Lepidopterous, Orthopterous, Dipterous and Hymenopterous insects is also described by Lovell.

The present invention provides solid, non-particulate, non-flowable, non-repellant, fully edible insecticide-bait compositions comprising from about 0.25% to about 5%, by weight, of a pentadienone substituted amidinohydrazone compound (I), in combination with a food attractant system, and a non-repellant water-soluble flowable binder. The insecticide-bait composition may further comprise a water-soluble preservative in order to, inter alia, enhance the shelf life of the composition.

Preferably, the invention provides such an insecticide-bait composition comprising an insecticide compound represented by formula (II), and particularly the compound 1,5-bis(2,2,2,-trifluoro-p-tolyl) -1,4-pentadien-3-one(1,4,5,6-tetrahydro-5,5-dimethyl-2-pyrimidinyl) hydrazone (III), wherein the groups X in formula (II) are each methyl. The insecticide-bait compositions of the invention, which are liquid at room temperature, may take any convenient form by pouring into molds, or bait trays and allowing to dry; such forms are wafers, pellets, molded caps, and the like.

The food attractant system used in the composition of the present invention comprises a mixture of a liquid food selected from the group consisting of molasses, corn syrup, maple syrup, honey, and mixtures of two or more of these foods. The amount of food attractant system and binder material used in the insecticide-bait compositions, and the ratio of one to the other, is not critical provided they form a cohesive solid at room temperature. Generally, the liquid food comprises about 20 to 50%, preferably 35 to 45%, by weight of the composition, and the oatmeal comprises about 25 to 75%, preferably 30 to 45%, by weight, of the composition.

The insecticide compound is, in general, not sufficiently soluble in the binder material. Although the solid insecticide compound may be incorporated into the binder in the form of discrete solid particles, it is preferable to convert the compound to a more readily dispersible form. It has been found that $C_8$–$C_{18}$ organic fatty acids are particularly useful in converting the insecticide into a form dispersible in the binder material. The fatty acid salt of the insecticide forms a dispersed internal phase in the continuous binder phase. Other acid salts, such as those obtained by reacting the insecticide with surfactants containing fatty acid groups, certain water-soluble acid salts such as acetates, lactates, propionates, sulfates, sulfonates, and the like, may also be useful in the dispersion of the insecticide in the binder. Generally the insecticide compound is dispersed by reaction with at least an equimolar amount of acid. Preferably, a molar excess of the acid is used. Preferred insecticide-bait compositions are obtained containing from about 1% to 3%, by weight, of the insecticide compound and 1% to 3%, by weight, of the fatty acid. Oleic acid is a preferred fatty acid.

As aforesaid, a suitable non-repellant preservative may also be incorporated into the composition to prevent spoilage thereof. When used, the preservative should be palatable to the cockroaches (dihydroacetic acid, for example, does not satisfy this requirement). A preferred preservative is the cis isomer of 1-(3-chloroallyl) 3,5,7-triaza-1- azonia-adamantane chloride, commercially available from Dow Chemical Company as Dowicil TM 200, and when used, it will generally comprise at least about 0.2%, preferably about 0.2 to 0.5%, by weight, of the composition.

The preferred compositions of the invention are advantageously used in a child and pet-resistance devise, which is, however, open and attractive to the insects. Such a device is described, for example, in commonly assigned, copending application, Ser. No. 406,671, filed Aug. 12, 1982, now abandoned and refiled as Ser. No. 681,079, filed Dec. 12, 1984, now abandoned and refiled as Ser. No. 180,718, filed Apr. 4, 1988, now U.S. Pat. No. 4,894,947.

Thus, it may be seen that the invention comprises a pourable liquid bait composition containing an aqueous polymer dispersion as binder, corn syrup or other sweetener as phagostimulant, and a suitable toxicant compound with suitable dispersant materials. Formulated bait liquid is poured into appropriate bait containers and solidifies by drying. Bait compositions in prior art are formed by pre-forming viscous material and subsequently inserting pre-formed mass into bait container. Current invention allows direct addition of material to bait container. Prior art compositions are semisolid during processing. Current invention is liquid during processing. "Pot-life" of formulation is many days, as compared with hours, in the case of prior art bait formulations. Direct addition of liquid composition to bait containers requires less -complex processing equipment, simpler process. The liquid may be mechanically or chemically foamed prior to container filling to reduce density of resulting solid bait. The invention can be applied to solid baits for use against any pest insect responding to sweetener phagastimulation, e.g. various cockroach spp. and various ant spp.

The invention is more completely described and illustrated by the following non-limiting examples, I to VII, shown in Table I.

The composition was tested against German cockroaches as described.

TABLE I

| CLASS | SPECIFIC INGREDIENT | RANGE | I | II | III | IV | V | VI | VII | VIII |
|---|---|---|---|---|---|---|---|---|---|---|
| PHASE A | | | | | | | | | | |
| ALCOHOL | ISOPROPANOL | 0.10–5.00 | 1.20 | 1.20 | 1.20 | 1.20 | 1.20 | 1.20 | 1.20 | 1.20 |
| FATTY ACID | OLEIC ACID | 0.10–5.00 | 1.20 | 1.20 | 1.20 | 1.20 | 1.20 | 1.20 | 1.20 | 1.20 |
| EMULSIFYING WAX | POLAWAX A-31 | 0.10–5.00 | 1.20 | 1.20 | 1.20 | | 1.20 | 1.20 | 1.20 | 1.20 |
| ACTIVE INGREDIENT | HYDRAMETHYLNON | 0.10–5.00 | 1.20 | 1.20 | 1.20 | 1.20 | 1.20 | 1.20 | 1.20 | 1.20 |
| PHASE B | | | | | | | | | | |
| GLUE | CASCOREZ WB 798 | 30.00–60.00 | 43.60 | 49.00 | | 31.90 | | | | |
| | COLLOID # I-V[1] | 30.00–60.00 | | | 34.90 | | 41.70 | | | |
| | DARATAK 17-200 | 30.00–60.00 | | | | | | | | 35.00 |
| | KNOX GELATINE[2] | 30.00–60.00 | | | | | | 21.50 | 46.70 | |
| CARBOHYDRATE | CORNSWEET 55 | 30.00–60.00 | 43.60 | 42.80 | 45.10 | 43.10 | 43.30 | 69.50 | 48.30 | 50.00 |
| POLYVINYL ALCOHOL, | | | | | | | | | | |
| EMULSIFIER | GELVATOL 3000 (15%) | 3.00–10.00 | 7.80 | 3.20 | 15.00 | | | | | |
| | VINOL 540 (5%) | 3.00–10.00 | | | | 20.00 | | 4.00 | | 10.003 |
| | VINOL 125 (5%) | 3.00–10.00 | | | | | 10.00 | | | |
| PRESERVATIVE | TEKTAMER 38 A.D. | 0.10–0.50 | 0.20 | 0.20 | | | | | | 0.20 |
| | DOWCIL 200 | 0.10–0.50 | | | | 0.20 | | | | |
| | COLLOID PRESER.[4] | 0.10–0.50 | | | | 0.20 | | 0.20 | 0.20 | 0.20 |
| | GLUE:SUGAR | 1:1–4:4 | 1:2 | 1:1.6 | 1:4 | 1:2.5 | 1:4 | 1:25 | 1:8 | 1:2 |

TABLE I-continued

| CLASS | SPECIFIC INGREDIENT | RANGE | I | II | III | IV | V | VI | VII | VIII |
|---|---|---|---|---|---|---|---|---|---|---|
| | EFFICACY, % MORTALITY | 94–100 | 99 | 99 | 97 | 98 | 95 | 96 | 94 | 99 |

[1] COLLOID # I-V is a 20% solution.
[2] KNOX GELATINE is a 10% solution.
[3] Used a 15% solution.
[4] Colloid Preservative is a mixture of 0.1% Zinc Sulfate, 0.05% Methyl Paraben, and 0.5% Butyl Paraben.

NOTES

Alcohol-methanol, ethanol, isopropanol, etc.
Fatty Acid- long chain fatty acid, vegetable oils, etc.
Emulsifying Wax-nonionic self emulsifying wax.
Active Ingredient- any common insecticide should work.
Glue- any natural or synthetic glue or polymer emulsion which can be poured cold or hot and would set in a reasonable amount of time.
Carbohydrate- corn syrup, glucose, molasses, sugar, etc.
Polyvinyl Alcohol- depending on the glue or polymer different grades of PVA have to be used. Also to have a more stable emulsion larger quantity of PVA has to be used.

PROCEDURE TO PREPARE BAIT

Mix ingredients of Phase A. Warm to melt Polawax and dissolve the active ingredient.
To a stirred solution of glue, polyvinyl alcohol and preservative, slowly add carbohydrate solution.
Stir until a homogeneous emulsion is obtained.
To the above emulsion, carefully add Phase A and stir until homogeneous.
Pour the bait solution in desired device and product will set in 2-3 hours.
The product was alternatively prepared by foaming before pouring the baits into the tray device. Foaming can be achieved by air by stirring. The resultant produce foamed sets faster and is also of lower density.

EFFICACY TESTING 40-50 Roaches (German) of mixed population (age and gender).
Greased sweater box, 11"×16" with harborage, alternate food and water.
Bait placed 24 hours after roach introduction.
Number of dead roaches counted after 7 days.

EXAMPLE VIII

In the following example, the comparative efficacy of a formulation, according to the present invention (Formula A), was tested against a formulation according to copending application Ser. No. 628,128. The formulations and results are shown as follows in Table II.

TABLE II

| | Formula A | Formula B |
|---|---|---|
| Isopropanol | 1.18 | 6.00 |
| Acid | 1.18 | Oleic 2.00 |
| Polawax A 31 | 1.18 | — |
| Hydtamethylon | 1.25 | 2.00 |
| Polyvinyl Acetate Emulsion | 35.00 | — |
| Cornsweet 55 | 50.00 | 40.00 |
| Polyvinyl Alcohol (15%) | 10.00 | — |
| Preservative (Vancide) | 0.21 (Tektamer) | 0.50 |
| Carbowax 8000 | — | 11.50 |
| Oatmeal | — | 38.00 |
| % Morality: Complex arena, | 39.60 | 34.50 |

TABLE II-continued

| | Formula A | Formula B |
|---|---|---|
| 7 day count, 8 replicates. Price per lb./% basis | 63% | 100% |

It will be seen that the product of the present invention was somewhat more efficaceous, and also less costly, as well as having the processing advantages of longer pot life, better pourability and less waste, as previously discussed.

What is claimed is:

1. A solid, non-particulate, non-repellant, insecticidal bait comprising by weight 0.25 to 5% of a non-repellant insecticide compound, a liquid food attractant, and a water-soluble binder material comprising a natural or synthetic glue and an emulsifier, said bait composition having a long pot life and being readily flowable during said pot life, and being non-flowable after being poured and hardened.

2. A solid, non-particulate, non-repellant, insecticidal bait composition, as claim 1, comprising about 0.25 to 5%, by weight, of an insecticide compound represented by the formula:

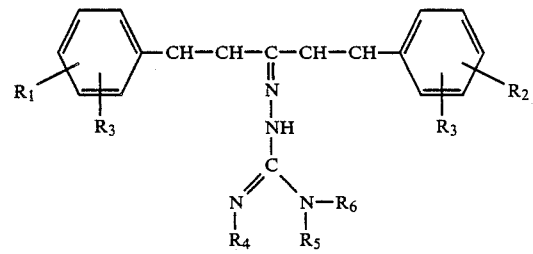

wherein $R_1$ and $R_2$ each represent hydrogen, halogen, —$CF_3$, $C_1$–$C_4$ alkyl, $C_1$–$C_4$ alkoxy, or $C_1$–$C_4$ alkylthio; $R_3$ is hydrogen or methyl, provided that when $R_3$ is methyl both $R_1$ and $R_2$ are also methyl; $R_4$ and $R_5$ represent hydrogen or $C_1$–$C_4$ alkyl or, when take together, an alkylene group of 2 to 6 carbon atoms, methyl or phenyl alkylene group of 2 to 4 carbon atoms or 1,2-cyclohexylene; $R_6$ is hydrogen or $C_1$–$C_4$ alkyl, and salts thereof, a food attractant comprising a liquid food selected from the group consisting of corn syrup, molasses, honey and maple syrup, and a water-soluble flowable binder material as in claim 1.

3. The composition of claim 2 wherein the insecticide compound is 1,5-bis(2,2,2-trifluoro-p-tolyl)-1,4-pentadiene-3-one(1,4,5,6-tetrahydro-5,5-dimethyl-2-pyrimidinyl)-hydrazone.

4. The composition of claim 1 wherein the binder material comprises a water-soluble polyvinyl acetate emulsion.

5. The composition of claim 1 wherein the food attractant system comprises corn syrup.

6. The composition of claim 1 further comprising a water-soluble preservative.

7. The composition of claim 1 further comprising as a water-soluble preservative the cis isomer of 1-(3-chloroallyl)-3,5,7-triaza-1-1-azonia-adamantane chloride.

* * * * *

UNITED STATES PATENT AND TRADEMARK OFFICE
CERTIFICATE OF CORRECTION

PATENT NO. : 4,990,514
DATED : February 5, 1991
INVENTOR(S) : Francis J. Bruey

It is certified that error appears in the above-identified patent and that said Letters Patent is hereby corrected as shown below:

In Table 1, bottom of Columns 3 & 4 under the column "RANGE" should read --1:1-1:4--.

Column 6, line 48, "4" should read --6--.

Signed and Sealed this

Ninth Day of March, 1993

Attest:

STEPHEN G. KUNIN

*Attesting Officer*      Acting Commissioner of Patents and Trademarks